| United States Patent [19] | [11] Patent Number: 4,766,205 |
| Ghosh-Dastidar | [45] Date of Patent: Aug. 23, 1988 |

[54] METHOD FOR ISOLATION OF RECOMBINANT POLYPEPTIDES IN BIOLOGICALLY ACTIVE FORMS

[75] Inventor: Pradip Ghosh-Dastidar, Los Angeles, Calif.

[73] Assignee: Beatrice Companies, Inc., Chicago, Ill.

[21] Appl. No.: 797,473

[22] Filed: Nov. 13, 1985

[51] Int. Cl.$^4$ .............................................. C07K 3/12
[52] U.S. Cl. ...................... 530/402; 530/408; 530/409; 530/344; 530/345; 530/412; 530/417; 530/370
[58] Field of Search ............... 260/112 R; 435/68; 530/350, 370, 402, 408, 409, 345, 344, 412, 417

[56] References Cited

U.S. PATENT DOCUMENTS

| | | | |
|---|---|---|---|
| 4,511,502 | 4/1985 | Builder et al. | 260/112 R |
| 4,511,503 | 4/1985 | Olson et al. | 260/112 R |
| 4,512,922 | 4/1985 | Jones et al. | 260/112 R |
| 4,518,526 | 5/1985 | Olson | 260/112 R |
| 4,530,787 | 7/1985 | Shaked et al. | 260/112 R |
| 4,569,790 | 2/1986 | Koths et al. | 260/112 R |

FOREIGN PATENT DOCUMENTS

| | | | |
|---|---|---|---|
| 136694 | 4/1985 | European Pat. Off. | |
| 0155832 | 9/1985 | European Pat. Off. | 435/68 |
| 3329624 | 3/1984 | Fed. Rep. of Germany | 435/68 |
| 83/04418 | 12/1983 | PCT Int'l Appl. | |
| 84/03711 | 9/1984 | PCT Int'l Appl. | 435/68 |
| 2138004A | 10/1984 | United Kingdom | |

OTHER PUBLICATIONS

Edens et al., "Cloning of CDNA Encoding ... Thaumatin ... E. Coli", Gene, 18, 1982, pp. 1–12.
Orsini et al., IBC 253(10), 1978, pp. 3453–3458.
Klausner, "And Then There Were Two", Biotechnology, vol. 3, pp. 605–614, Jul. (1985).
Lehninger, Principles of Biochemistry, 177–179 (1982).
Odorzynski and Light, "Refolding of Mixed Bovine Trypsinogen and Glutathione", J. Biol. Chem., vol. 254, No. 10, pp. 4291–4295 (1979).
Smithies, "Disulfide–Bond Cleavage and Formation in Proteins", Science, vol. 150, pp. 1595–1598 (1965).
Stryer, Biochemistry, 32–36 (2d Ed. 1981).
Wetzel et al., "Expression in *Escherechia coli* of a Chemically Synthesized Gene for a 'Mini-C' Analog of Human Proinsulin", Gene, 16, pp. 63–71 (1981).

*Primary Examiner*—John Kight
*Assistant Examiner*—Garnette D. Draper
*Attorney, Agent, or Firm*—Marshall, O'Toole, Gerstein, Murray & Bicknell

[57] ABSTRACT

Disclosed are improved methods for orienting polypeptide molecules containing multiple disulfide bonds into their native conformation through (1) treating the polypeptide with (a) a denaturing agent and (b) a reducing agent capable of reductively dissociating cystine disulfide bonds; (2) concurrently reducing the concentration of the reducing agent while forming a stable intermediate by reacting a disulfide containing compound with the reduced cysteine moieties of the polypeptide and; (3) forming native cystine disulfide bonds in the presence of a mild oxidizing/reducing environment while dissociating the disulfide-group polypeptide moeities.

12 Claims, No Drawings

METHOD FOR ISOLATION OF RECOMBINANT POLYPEPTIDES IN BIOLOGICALLY ACTIVE FORMS

BACKGROUND OF THE INVENTION

The present invention relates generally to procedures for preparing biologically active polypeptide products and more particularly to procedures for establishing a biologically active natural conformation in polypeptides containing multiple disulfide bonds.

In the recent past substantial advances have been made in recombinant DNA procedures for securing synthesis of a wide variety of polypeptide products in microorganisms, including bacteria, yeast and mammalian cells in culture. "Foreign" polypeptides can now rather readily be expressed in relatively high yields in genetically transformed host cell cultures, either as discrete polypeptides or as fusion polypeptides including the desired polypeptide linked in sequence to a second, usually endogenous, polypeptide such as β-galactosidase.

These advances in securing expression of polypeptides have given rise to an entire new series of problems relating to recovery of desired polypeptide products from microorganisms in useful forms. Apart from the general difficulties inherent in isolating polypeptide products away from native host cell proteins, recovery problems are particularly significant in microbial systems employed for synthesis of biologically active polypeptides such as human growth hormone, interferons and the like, where the biological activity (and potential utility) of the recovered polypeptide product is dependent upon the product's assumption of secondary and tertiary structural conformations duplicative of naturally occurring forms.

A polypeptide exists as a chain of amino acids linked by peptide bonds. In the normal biologically active form of a polypeptide (hereinafter referred to as the native form) one or more chains are folded into a thermodynamically preferred three dimensional structure, the conformation of which is determined by steric considerations, the existence of covalent disulfide bonds, if any, and noncovalent interatomic forces such as charge influences, hydrogen bonding and hydrophobic interactions. The amino acid cysteine contains a sulfur atom which is capable of forming cystine disulfide bonds with other cysteine residues. These bonds are capable of forming on an intra- or interchain basis and play a key role in establishing a stable tertiary structure for many polypeptides.

In the isolation of polypeptide products from recombinant host cells, it is often the case that recovered polypeptides fail to adopt their native conformation and, as a result, are biologically inactive with respect to certain desired properties. It is thought that this occurs because the cellular environment of the recombinant host often does not provide conditions in which the proper "folding" of the foreign polypeptide can spontaneously occur after synthesis. However, since it is a generally accepted tenet that information dictating the tertiary structure of polypeptides resides in their primary sequence, such inactive polypeptides can occasionally be induced to adopt their biologically active "native" structure by a simple denaturation and renaturation process. A denaturing agent can be added to a polypeptide which will disrupt the noncovalent interatomic forces and effectively "unfold" the molecule. The polypeptide can then be renatured by removal or dilution of the denaturing agent so that the polypeptide adopts its native conformation.

In many cases, however, biologically inactive polypeptides represent molecules which are "frozen" in a non-native conformation because of the formation of non-native cystine disulfide bonds. These bonds frequently occur during polypeptide expression in host organisms before the polypeptide molecule adopts its favored native conformation. With increasing numbers of cysteine residues in a polypeptide, the probability that disulfide bonds will properly form decreases exponentially. Once non-native bonds form, however, the polypeptide is effectively locked out of its native conformation. Because disulfide bonds are covalent, polypeptides possessing non-native structures as a result of incorrect cystine bond formation are not readily susceptible to reformation by a simple denaturation/renaturation procedure.

The difficulties associated with recovery of biologically active polypeptides containing multiple disulfide bonds have been so severe that in a few instances new polypeptide analogs of significant proteins have been "designed" for microbial expression on the basis of their greater potential for recovery in a biologically active state rather than for possibly enhanced or prolonged activity. As one example, the general inability to recover a beta interferon polypeptide (three cysteine residues) in biologically active form prompted construction of genes for expression of various des-cysteine analogs wherein undesired disulfide bond formation was precluded by limiting the number of cysteine residues available for such reactions from three to two. Mark, et al., "The Effects of Site Specific Mutation on the Biological Activity of Human Fibroblast Interferon", Abstract, Second International T.N.O. Meeting on the Biology of the Interferon System, Antiviral Research (1983). For polypeptides with two or more cystine bonds, however, such techniques will be limited in their effectiveness.

Workers have utilized several methods to reform native conformations in multiple disulfide bond polypeptides. The simplest of these involve techniques whereby a polypeptide molecule is denatured, its cystine disulfide bonds are reductively cleaved, native disulfide bonds are allowed to form and the polypeptide is renatured to its native conformation. Stryer, *Biochemistry*, 32–36 (2d Ed. 1981), describes work on denaturing and reforming the native conformation of ribonuclease, a protein with a single polypeptide chain consisting of 124 amino acid residues and having four disulfide bonds. It was noted that natural ribonuclease in its properly folded form could be denatured by exposure to a concentrated urea solution in the presence of a reducing agent such as β-mercaptoethanol which cleaves the four disulfide bonds to yield eight cysteine residues. The denatured compound was completely uncoiled and exhibited no enzymatic activity. The reduced ribonuclease solution was dialyzed allowing the urea and reducing agent to diffuse away from the polypeptide. Upon air oxidation of the reduced cysteine residues in the ribonuclease, the polypeptide spontaneously refolded into its native conformation and the native disulfide bonds reformed as determined by a return of catalytic activity.

Other methods are also known for establishing native conformations in microbiologically-produced disulfide containing polypeptides. Lowe, et al. U.K. patent application No. 2,138,004A discloses variations on the above process whereby polypeptides may be denatured and their disulfide bonds reduced in the presence of denaturing agents such as guanidine hydrochloride or urea used in combination with an alkali reducing agent. Guanidine hydrochloride and urea are capable of denaturing a polypeptide chain but are incapable of cleaving disulfide bonds. Conversely, a strong alkali solution is capable of reductively dissociating disulfide bonds but may not alone be capable of completely denaturing some polypeptides. According to the procedure of Lowe, et al., a polypeptide is first denatured in an aqueous solution with guanidine hydrochloride or urea and is then diluted in an alkaline aqueous solution at a pH selected to promote dissociation of the group or groups of the polypeptide involved in maintaining the non-native conformation of the polypeptide. The polypeptide is then renatured by reducing the pH of the solution below a pH effective to denature the polypeptide to produce the native conformation. The method is disclosed to produce satisfactory results when applied to the protein prochymosin, a monomeric protein containing three intramolecular disulfide bonds. Reduction of the cystine bonds can be achieved by using an alkaline aqueous solution of pH 10.7 ($\pm 0.5$) as these workers state that the free thiol groups of cysteine in prochymosin have a pKa value of 10.46.

Use of pH based procedures for denaturation and renaturation of polypeptides is not without its limitations, however. Extreme low or high pHs can irreversibly denature polypeptides by reacting with amino acid residues making up the structure. Care must also be taken that denatured and reduced polypeptides do not prematurely reoxidize and renature. Even if a polypeptide is completely denatured and its disulfide bonds completely reduced, it is possible that cysteine residues may spontaneously reoxidize to form non-native conformations. This can be a particular problem where the polypeptide solution is a fairly concentrated one and reactive cysteine residues can easily associate with cysteine residues from other molecules to form dimers.

Some workers have sought to prevent spontaneous non-native bonding by forming intermediate adducts with the reduced cysteine residues. The reduced cysteine residues are reacted in an oxidation reaction with a disulfide containing compound which prevents the cysteine residue so reacted from reacting with other cysteine residues on the same or other polypeptide molecules. The polypeptide solution may then be diluted into a buffer containing a weak reducing agent, the disulfide group intermediates reduced and the polypeptide molecules allowed to slowly renature to their native conformation. The fact that the polypeptide molecules are "protected" from reaction until they are diluted, substantially raises the probability that the polypeptides will renature to their native conformation.

Among intermediate forming techniques known in the art, Wetzel, et al., *Gene*, 16, pp. 63–71 (1981), describes efforts directed toward purification of a "mini-C proinsulin" product from a culture system involving *E. coli* expression of a $\beta$-galactosidase fusion protein. The fusion polypeptide was harvested and was treated with cyanogen bromide to cleave the proinsulin product from the fusion protein. The cleaved proinsulin product was solubilized with guanidine hydrochloride denaturing agent and treated with sodium sulfite and sodium tetrathionate reducing agents in order to form a stable "S-sulfonate" oxidized reaction product at the site of the cysteine residues in the polypeptide. The resulting mini-C proinsulin S-sulfonate product was thereafter further processed with a $\beta$-mercaptoethanol reducing agent at 0° C. and under a nitrogen atmosphere to dissociate the covalently-bound sulfonate groups. This prompted formation of native disulfide bonds and allowed assumption of the tertiary structure needed for achievement of biological activity.

Numerous variations on the above-mentioned techniques are also known in the art. Builder, et al. U.S. Pat. No. 4,511,502, Olson, et al. U.S. Pat. No. 4,511,503 and Jones, et al., U.S. Pat. No. 4,512,922 disclose the use of "strongly denaturing solutions" comprising guanidine hydrochloride or sodium thiocyanate in high concentrations of approximately 4–9M or detergents such as sodiumdodecyl sulfate (SDS) or Triton-X-100 in concentrations of about 0.01 to about 2%. Also disclosed are "weakly denaturing solutions" comprising either urea or the materials of strongly denaturing solutions at lesser concentrations. Among the reducing agents disclosed are $\beta$-mercaptoethanol, dithiothreitol and reduced glutathione. Compounds disclosed for disulfide adduct formation include oxidized glutathione, cystamine and cystine. A disulfide adduct forming renaturation technique is disclosed whereby a polypeptide is denatured in a strong denaturing solution containing a reducing agent which reductively dissociates any disulfide bonds. The polypeptide is then treated with a mild oxidizing agent in the presence of sulfite ion to form disulfide adducts. The strong denaturing solution is then replaced with a weakly denaturing solution to permit refolding, and disulfide linkages are reformed using sulfhydryl compounds such as, for example, cysteine or reduced glutathione, in the presence of the corresponding oxidized (disulfide) form, but with the reduced form in excess.

Also known is a "simultaneous" unfolding and refolding procedure whereby a polypeptide is placed into a sulfhydryl/disulfide-containing buffer, which buffer has sufficient denaturing power that all of the intermediate conformations remain soluble in the course of unfolding and refolding. Both reduced and oxidized (disulfide) forms of sulfhydryl compounds are disclosed to be in the medium. In this redox buffer refolding procedure, the molar ratio of reduced to oxidized forms of sulfhydryl compounds is disclosed to be from 5:1 to 20:1. The pH must be sufficiently high so as to assure at least partial ionization of the sulfhydryl groups but not so high as to irreversibly denature the polypeptide.

In recent years much work has been directed toward recombinant microbial synthesis of the extremely sweet polypeptide thaumatin. Thaumatin is produced in the arils of the fruit of the African shrub *Thaumatococcus daniellii* Benth. The fruit traditionally has been used in West Africa as a sweetener of palm wine, corn, bread and sour fruit. Thaumatin, which is about 5000 times sweeter than sucrose on a weight basis, is produced in at least five forms: thaumatins I, II, a, b and c. These polypeptides, named in their order of elution from an ion exchange column [Higgenbotham, et al., in *Sensory Properties of Foods* (Birch, et al., eds.), London: Applied Sciences, pp. 129–149 (1977)], have molecular weights of approximately 22 kilodaltons.

Thaumatins I and II are non-toxic polypeptides, are low-calorie and non-cariogenic, and elicit profound sweet taste responses suggesting a stable interaction between these polypeptides and human taste buds.

Therefore, thaumatin has potential for use as a sugar substitute, food additive, a sweetness receptor probe and a tool for further elucidation of the taste response.

A plentiful supply of pure thaumatin is required to utilize the protein as a possible food additive and research tool. Because the thaumatin plant requires a tropical climate and insect pollination for successful fruit propagation, there are considerable difficulties involved in greenhouse cultivation of the fruit. For these reasons, considerable effort has been directed toward the introduction of genes into recombinant microorganisms enabling them to synthesize thaumatin. One research group has reported the successful cloning of a gene for thaumatin II from messenger RNA-derived cDNA [Edens, et al., Gene, 18, 1-12 (1982)]. The Edens, et al. reference cited above notes that a polypeptide having the native sequence of preprothaumatin II has been microbially produced. More specifically, the reference and European patent application Nos. 54,330 and 54,331 disclose cDNA sequences coding for native mature thaumatin II and preprothaumatin II and also disclose cloning vehicles comprising the DNA sequences for use in transformation in microorganisms.

In co-owned and copending U.S. patent application Ser. No. 540,634 filed Oct. 11, 1983, now abandoned, the successful synthesis of "manufactured" genes coding for thaumatin I having a primary structural conformation duplicating the sequence provided in Iyengar, et al. Eur. J. Biochem., 96, 193-204 (1979) was disclosed along with their expression in bacterial and yeast hosts. The polypeptides that have been expressed contain the primary conformation (amino acid sequence) of thaumatin I but are not always sweet and often do not exhibit the secondary and tertiary conformations of the native polypeptide. It is believed that similar difficulties plague other workers in the field.

The failure of the recombinant-produced thaumatin to adopt the native conformation and activity of plant produced thaumatin is believed to result from the different cellular milieu found in the recombinant organism. The solubility, pH and electronic environment of the recombinant host cell is such that the thaumatin adopts a conformation lacking biological activity. Conventional methods for establishing the native conformation and biological activity demonstrate only limited success. A complex globular structure postulated for the thaumatin molecule is disclosed in de Vos, et al., Proc. Natl. Acad. Sci., 82, 1406 (1985), which shows 16 cysteine residues combining to form 8 specific disulfide bonds. This large number of cystine bonds makes folding to the native structure extremely difficult.

The difficulty in establishing native conformations in thaumatin and other polypeptides containing high numbers of disulfide bonds when using traditional adduct forming techniques, stems, at least partially, from premature reoxidation of cysteine residues to form non-native disulfide bonds during the adduct formation step. Between the step of denaturing the polypeptide and reducing any existing disulfide bonds and the step of introducing disulfide group containing compounds to form the disulfide adduct, the concentration of the reducing agent is often reduced in conventional adduct forming methods. During the period while the concentration of the reducing agent is being reduced and before intermediate adducts have been formed on the reduced cysteine residues, many of the cysteine residues will spontaneously oxidize with other cysteine residues to form non-native disulfide bonds. Once such incorrect bonds have been formed, they may preclude the polypeptide from assuming its correct conformation.

Accordingly, there exists a need in the art for techniques for generating biologically active native conformations of polypeptides, especially recombinant-produced polypeptides with multiple cysteine residues. The techniques should be efficient, producing a high yield of polypeptide in its correct conformation and should be relatively rapid.

BRIEF SUMMARY

The present invention provides a new, rapid and efficient method for establishing biologically active native conformations in polypeptides derived from natural and recombinant sources which contain multiple disulfide bonds. In accordance with the present invention, it has been found that concurrently removing the reducing agent from a solution of denatured and reduced polypeptide while forming a stable polypeptide intermediate adduct by reaction of reduced cysteine moieties with disulfide containing compounds results in a faster and more efficient process for establishing biologically active native conformations in polypeptides containing multiple disulfide bonds.

More specifically, it has been found that concurrently reducing the concentration of the reducing agent in a solution of denatured and reduced polypeptide while introducing disulfide containing compounds increases the probability that individual reduced cysteine residues will reoxidize to form stable intermediate adducts with the introduced disulfide compounds rather than with other cysteine polypeptide residues. By maintaining a gradient of concurrently decreasing reducing agent concentration and increasing adduct-forming disulfide group concentration only a few reduced cysteine residues are capable of oxidizing at any given time. This ensures that they are more likely to react with the introduced adduct forming disulfide compounds than with each other. Once the individual cysteine residues have reacted with the adduct-forming disulfide compounds, they are incapable of reacting with (and possibly forming incorrect non-native bonds with) other reduced cysteine residues which subsequently (with further removal of the reducing agent) become capable of reaction. The concurrent and relatively gradual removal of reducing agents also helps in the formation of biologically active polypeptides by protecting sensitive amino acid residues such as methionine and tryptophan from oxidative degradation.

After formation of the stable adduct, the native cystine bonds may be reformed and the polypeptide refolded to its native conformation in the presence of a mild oxidizing/reducing environment which can comprise a weak reducing agent and a weak oxidizing agent in the presence of a suitable pH. The adduct may be diluted into an oxidizing buffer containing a weak reducing agent so that the protecting sulfhydryl groups are cleaved. The cysteine groups can now reoxidize to form native disulfide bonds during which the polypeptide gradually assumes its native conformation. Weak reducing agents suitable for such treatment include cysteine, reduced glutathione and cysteamine. Weak oxidizing agents suitable for such treatment include atmospheric oxygen, cystine, oxidized glutathione and cystamine. The mild oxidizing/reducing environment must be balanced such that it is sufficiently reducing to reduce the disulfide adduct bonds and any nonnative disulfide bonds yet sufficiently oxidizing to allow formation of native cystine bonds so as to provide reformation of the native polypeptide conformation. To this end a pH greater than about 7 has been found to be advantageous with a pH between about 7 and about 9 especially suitable. Other aspects and advantages of the present invention will be apparent upon consideration of the following detailed description of its practice.

DETAILED DESCRIPTION

Practice of the improved recovery procedures of the invention involves the initial step of isolating polypeptide products, including recombinant protein products, from natural sources or recombinant host cells. This can readily be accomplished by any conventional means such as lysis of the cells (e.g., by high pressure disruption, sonication, freezing and thawing, lysozyme or detergent treatment or the like) followed by centrifugation.

Following the initial isolation step, the fraction containing the desired polypeptide may be denatured and solubilized by a variety of means. The polypeptide may be treated with high pH, urea, guanidine sulfate, guanidine hydrochloride, sodium thiocyanate, potassium thiocyanate or other salts or the like. [*Methods in Enzymology*, 22, pp. 210–213 (1971)].

The material solubilized by any of these methods is then treated with a suitable reducing agent such as a mono-, di-, or poly-functional sulfhydryl-group containing agent such as β-mercaptoethanol or dithiothreitol. Also useful are sodium borohydride, sodium cyanoborohydride or organohydrido borates such as sodium methylhydrido borate. Most preferred is use of β-mercaptoethanol in concentrations of from 1 mM to 1M. These materials operate to reductively dissociate disulfide bonds extant in the solubilized and denatured polypeptide.

Following denaturation and reduction of the disulfide bonds the reducing agent is removed concurrent with introduction of disulfide containing adduct-forming compounds. The disulfide containing compounds react with the reduced cysteine residues to form stable intermediate adducts concurrently with the removal of the reducing agent. Suitable disulfide adduct forming compounds include cystamine, oxidized glutathione, cystine, sodium sulfite salts and the like. Most preferred is cystamine at a concentration of about 100 mM although oxidized glutathione at a concentration of about 100 mM also provides satisfactory results. The concurrent reducing agent removal and adduct formation is preferably carried out in a gel filtration column. The column, which can be packed with filtration gels such as Sephadex G-25, is equilibrated with a denaturing agent, an adduct forming disulfide compound, as well as a suitable buffer solution such as Tris-HC. Most preferred is a Sephadex G-25 column equilibrated with 50 mM Tris-HCl (pH 9), 6M urea and 100 mM cystamine.

The denatured and reduced polypeptide solution is eluted through the column. The reduced polypeptide fraction gradually elutes away from the reducing agent fraction such that the concentration of the reducing agent in the polypeptide fraction gradually decreases. Concurrently, as the polypeptide fraction elutes through the gel column, it contacts the adduct forming disulfide compounds. These compounds react with the reduced cysteine moeities of the polypeptide to form stable intermediate disulfide adducts. This adduct formation occurs concurrently with removal of the reducing agent such that over time there is a gradient of polypeptides extending from those which are reduced and do not contain disulfide adducts to those which are fully oxidized and have all of their cysteine residues in the adduct group form.

Fractions eluting from the column are collected and the polypeptide containing fractions may be located utilizing protein assays. The polypeptide adduct fraction is isolated and concentrated and the pH lowered to 4. The polypeptide adduct fraction is then run through a gel filtration column again to remove excess cystamine and is diluted to 20 μg/ml into a cold (4° C.), aqueous solution comprising a weak reducing agent (preferably 2 mM cysteine) which cleaves the disulfide adduct bonds. Practice of this treatment step according to the invention is preferably carried out under solution pH conditions at or above neutrality to insure that the cysteines and any sulfhydryl-containing reagents are at least partially ionized. The polypeptide is then dialyzed against an aqueous solution of 0.1 M $NH_4HCO_3$ and then against pure water to allow removal of excess cysteine, cysteamine, and buffering agents. Alternatively, the polypeptide solution is passed through a 100,000 molecular weight cutoff membrane filtration system. The eluate is then concentrated and washed with $H_2O$ on a 10,000 molecular weight cut off membrane filtration system.

EXAMPLES 1–5

In these examples, natural plant thaumatin comprising a mixture of the I, II, a, b and c varieties in their native forms was reduced and denatured and was then refolded under varying conditions, via an intermediate adduct form, to its native conformation.

Ten mg of the plant thaumatin (obtained from Sigma Chemical Co., St. Louis, MO) was dissolved in 1 ml of 6M urea and was reduced for two hours at 37° C in the presence of 0.2M of β-mercaptoethanol in a 0.1M Tris-HC buffered solution with a pH of 9. At the same time, a 1.5 cm×28 cm Sephadex G-25 gel filtration column was equilibrated with 6M urea, 50 mM Tris HCl (pH 9) and 100 mM cystamine. After being reduced and denatured for two hours, the thaumatin solution was applied to the gel filtration column. The eluted fractions were checked for protein by a Bio-Rad protein assay sampling 20 μaliquots from each 1 ml fraction.

The peak fractions of treated thaumatin were pooled together and concentrated by Amicon YM-5 ultrafiltration. The cystamine-thaumatin adduct was then allowed to stand for 3 hours in a nitrogen purged 100 mM cystamine solution. After 3 hours the adduct (7 mg of thaumatin, 2 ml in volume) was acidified with acetic acid to pH 3.5 and was loaded onto a second Sephadex G-25 column (1.5 cm by 24 cm) which had been equilibrated with 0.1N acetic acid and 0.1 mM EDTA. The elution of thaumatin was monitored by optical density at a wavelength of 280 nm and 5 ml of the peak fractions were pooled.

In Examples 1–3, the thaumatin adduct was then diluted to a concentration of 20 μg/ml in 50 ml tubes containing 50 mM·Tris HCl (pH 8) and either 0, 2 or 4 mM cysteine. In Examples 4 and 5, the adduct was diluted to a concentration of 50 μg/ml and was placed in 50 ml tubes containing 50 mM Tris HCl (pH 8), 2 mM cysteine and either 10 or 20% glycerol. The tubes were incubated overnight in an ice bath.

The following morning each of the thaumatin adducts contained in the tubes was dialyzed against 0.1M NH$_4$HCO$_3$ for three hours. This was followed by dialysis against water for 6 hours with 5 water changes during that time. For each example, the amount of purified thaumatin polypeptide recovered was measured and a taste test was conducted. Results for the five samples are shown in Table 1.

TABLE 1

| Example No. | Treatment | Dilution Concentration (µg/ml) | Polypeptide Recovered (µg/ml) | Sweetness |
|---|---|---|---|---|
| 1 | 0 mM cysteine | 20 | 14.5 | — |
| 2 | 2 mM cysteine | 20 | 15 | + |
| 3 | 4 mM cysteine | 20 | 7.5 | + |
| 4 | 2 mM cysteine 10% glycerol | 50 | 26 | + |
| 5 | 2 mM cysteine 20% glycerol | 50 | 24 | + |

Samples from Examples 2–5 demonstrated a sweet taste upon tasting. Only the sample from experiment 1 which was not treated with cysteine failed to exhibit a sweet taste. Example 2 utilizing 2 mM cysteine and containing no glycerol demonstrated the highest polypeptide recovery when taking the initial dilution concentrations into effect.

EXAMPLE 6

In this example, a recombinant yeast produced thaumatin analogue produced according to the method of co-owned and co-pending U.S. application Ser. No. 797,474 for "DNA Encoding [Asp$^{113}$] and [Lys$^{46}$, Asp$^{113}$] Thauamtin I," and having a lysine amino acid residue at position 46 of the polypeptide chain and an aspartic acid residue at position 113 of the polypeptide chain ([Lys$^{46}$, Asp$^{113}$] thaumatin I) was refolded and successfully tested for sweetness. Thirty mg of the recombinant thaumatin was dissolved in a 3 ml of solution comprising 8M urea, 0.2M β-mercaptoethanol and 0.1M Tris-HCl buffer (pH 9). The thaumatin had previously been determined not to be sweet. The thaumatin was then reduced for two hours at a temperature of 37° C.

At the same time, a 2.0 cm by 22 cm Sephadex G-25 gel filtration column was equilibrated with 6M urea, 50 mM Tris-HCl (pH 9) and 50 mM cystamine. After being reduced and denatured for two hours, the thaumatin solution was applied to the gel filtration column. The peak fractions of treated thaumatin eluting from the column were pooled and concentrated to 3 ml on a YM10 filter and allowed to stand at room temperature for 3 hours. The thaumatin was then loaded onto a second 2.0 cm by 22 cm Sephadex G-25 column and the eluents were collected in 1 ml fractions. The elution of thaumatin was monitored by measuring optical density at 280 nm. Seventeen mg of the thaumatin was then diluted into 850 ml of refolding solution containing 50 mM Tris-HCl (pH 8) and 2 mM cysteine and allowed to stand overnight at 4° C. The thaumatin solution was then dialyzed against 0.1M NH$_4$HCO$_3$ for three hours followed by dialysis against water for 6 hours with 5 water changes during that time. The final polypeptide concentration in the solution was 6 µg/ml. A taste test was conducted on the refolded polypeptide and it was found to be sweet.

EXAMPLE 7

In this example, the [Lys$^{46}$, Asp$^{113}$] recombinant thaumatin analogue was refolded to its sweet native conformation in a procedure utilizing glutathione as its disulfide group adduct forming agent. Five mg of the [Lys$^{46}$, Asp$^{113}$] recombinant thaumatin was dissolved in 0.5 ml of 8M urea and was reduced for three hours at 37° C. in the presence of 0.2M β-mercaptoethanol in a 0.1M Tris-HCl buffered solution (pH 9). At the same time, a 2.0 cm by 22 cm Sephadex G-25 gel filtration column was equilibrated with 6M urea, 50 mM Tris-HCl (pH 9) and 100 mM oxidized glutathione. After being reduced and denatured for two hours, the thaumatin solution was applied to the gel filtration column. The peak fractions of treated thaumatin eluting from the column were pooled and concentrated to 3 ml on a YM10 filter and allowed to stand at room temperature for 3 hours. The thaumatin was then loaded onto a second 2.0 cm by 22 cm Sephadex G-25 column and the eluents were collected in 1 ml fractions. The elution of thaumatin was monitored by measuring optical density at 280 nm. Four mg of the thaumatin was then diluted into 200 ml of refolding solution containing 50 mM Tris-HCl (pH 8) and 2 mM cysteine and allowed to stand overnight at 4° C. The thaumatin solution was then dialysed against 0.1M NH$_4$HCO$_3$ for three hours followed by dialysis against water for 6 hours with 5 water changes during that time. The final polypeptide concentration in the solution was 5 µg/ml. A taste test was conducted on the refolded polypeptide and it was found to be sweet.

EXAMPLE 8

In this example, the [Lys$^{46}$, Asp$^{113}$] recombinant thaumatin I analogue was treated by a conventional refolding procedure not contemplated by the invention. The procedure utilized β-mercaptoethanol as a reducing agent and glutathione as a disulfide group-adduct forming agent but did not utilize the method of the invention comprising concurrently reducing the concentration of the reducing agent while forming a stable intermediate by reacting a disulfide containing compound with the reduced cysteine moeities of the polypeptide.

In this example, 5 mgs of the thaumatin I analogue was denatured and reduced at a concentration of 10 mgs/ml for 4 hours at 37° C. in a nitrogen blanketed solution comprising 8M urea, 0.1M Tris-HCl buffer (pH9) and 0.2M β-mercaptoethanol. The solution was then run through a Sephadex G-25 gel filtration column pretreated with acetic acid to lower the pH to 4 and the eluate was fractionated in a solution comprising 8M urea and 0.1N acetic acid. The reduced thaumatin was then pooled and added to a solution comprising 0.1M oxidized glutathione, 10$^{-6}$M leupeptin and 0.1 M Tris-HCl buffer (pH9). The solution was flushed with nitrogen and incubated for 16 hours at room temperature in order to form a thaumatin-glutathione adduct.

The solution was dialyzed overnight against 0.1M acetic acid at 4° C. and freeze-dried. The material was then redissolved in a solution comprising 8M urea and 0.1M acetic acid at a concentration of 10 mgs/ml. Three mgs of the thaumatin was then diluted in 150 ml of refolding buffer comprising 50 mM Tris-HCl (pH8) and 2 mM cysteine and incubated overnight at 4° C. The thaumatin was dialyzed once against a 0.1M NH$_4$HCO$_3$ solution and four times against pure water. The final solution comprised 125 ml of thaumatin at a concentration of 0.25 µg/ml. A taste test was conducted on the thaumatin and no sweetness was detected. The material had to be concentrated 24 times by lyophilization before a sweet taste could be detected.

A radioimmunoassay (RIA) procedure was carried out to determine the extent of refolding of the thaumatin analogue. The assay procedure was developed using polyclonal antibodies in antiserum produced in rabbits which are specifically reactive with the sweet refolded form of thaumatin at a dilution of 1:70,000. For thaumatin renaturation experiments, the ratio of immunologically cross-reactive material to the total protein remaining in solution gave the percent refolding of the thaumatin-adduct to native thaumatin. In this example, 0.145 μg/ml of the thaumatin present in the final solution was reactive with the radioimmunoassay. Based on 3 mg of thaumatin adduct this indicates that roughly only 1% of the thaumatin adduct was successfully refolded into its sweet form.

EXAMPLES 9-11

In these examples, recombinant yeast produced [Asn$^{113}$] thaumatin I having an amino acid sequence duplicating the sequence provided in Iyengar, et al. and natural plant thaumatin I (obtained from Sigma Chemical Co.) were refolded according to the procedure of Example 2 utilizing cystamine as a disulfide compound and 2 mM cysteine as a mild reducing agent in the refolding step. A taste test was conducted on the thaumatin materials before refolding, with the plant thaumatin found to be sweet but the recombinant thaumatin found not to be. Refolding procedures were run on 5 mg each of [Asn$^{113}$] thaumatin I (Example 9), plant thaumatin I (Example 10) and a 1:1 by weight mixture of the two (Example 11). The refolded products were tasted for sweetness with the results that the refolded plant thaumatin elicited a very sweet taste, the refolded [Asn$^{113}$] recombinant thaumatin did not elicit a sweet taste and the 1:1 mixture of the two elicited a moderately sweet taste.

EXAMPLES 12-13

In these examples recombinant [Asn$^{113}$] thaumatin I duplicating the sequence provided in Iyengar, et al. and natural plant thaumatin I obtained from Sigma Chemical Co. were treated according to the refolding procedure of Example 7 which utilizes glutathione as its adduct forming agent. Five mg of recombinant [Asn$^{113}$] thaumatin I and natural plant thaumatin I were each dissolved, reduced and treated in gel filtration columns according to the procedure in Example 7.

After lyophilization of the glutathione adducts eluting from the gel filtration columns 3.2 mg of plant thaumatin I and 3.05 mg of recombinant [Asn$^{113}$] thaumatin I were redissolved in an 8M urea and 0.1N acetic acid solution at 10 mg/ml and were diluted to a concentration of 20 μg/ml in solutions of 50 mM Tris-HCl (pH 8.3) and either 1 mM or 2 mM cysteine. The polypeptide solutions were then incubated overnight at 4° C. Each of the thaumatin solutions were then dialyzed against 0.1M NH$_4$HCO$_3$ for 8 hours followed by dialysis against H$_2$O for 16 hours. Seven hundred μg of refolded recombinant [Asn$^{113}$] thaumatin was recovered which was determined to be not sweet while 962 μg of refolded plant thaumatin was recovered which was determined to be sweet.

EXAMPLES 14-16

In these examples, a radioimmunoassay according to the procedure of example 8 was carried out on three types of recombinant produced thaumatin I materials refolded according to the invention. The materials tested were [Asn$^{113}$] thaumatin I according to the sequence of Iyengar, et. al., [Asp$^{113}$] thaumatin I analogue and [Lys$^{46}$, Asp$^{113}$] thaumatin I analogue. The materials were refolded according to the cystamine procedure of example 6 and each refolding procedure was conducted with thaumatin-cystamine adduct concentrations of 20 μg/ml. Radioimmunoassays were conducted on the refolded materials to determine refolding efficiencies and taste tests were also conducted on the materials. Thaumatin with the [Asn$^{113}$] Iyengar, et al. sequence had a refolding efficiency of less than 1% while the [Asp$^{113}$] thaumatin I analogue had a refolding efficiency of about 6% and the [Lys$^{46}$, Asp$^{113}$] thaumatin I analogue had a refolding efficiency of about 12%. Taste tests failed to indicate a sweet taste for the Iyengar, et al. and only one of seven individuals detected a sweet taste for the [Asp$^{113}$] thaumatin I analogue, while five of seven individuals detected a sweet taste for the [Lys$^{46}$, Asp$^{113}$] thaumatin I analogue. Upon concentration by lyophilization, however, all those who tasted the materials were able to detect a sweet taste with the [Asp$^{113}$] and [Lys$^{46}$, Asp$^{113}$] thaumatin I analogues although again none were able to detect a sweet taste for the concentrated [Asn$^{113}$] thaumatin according to the sequence of Iyengar, et al.

TABLE 2

| Example No. | Thaumatin Type | RIA Reacted (μg/ml) | Refolded/ Started (%) | Sweetness |
| --- | --- | --- | --- | --- |
| 14 | [Asn$^{113}$] | 0.1 | 0.5 | − |
| 15 | [Asp$^{113}$] | 1.3 | 6.5 | + |
| 16 | [Lys$^{46}$, Asp$^{113}$] | 2.4 | 12.0 | + |

EXAMPLES 17-22

In this set of examples, samples of natural plant thaumatin I in its native conformation and recombinant produced thaumatin I analogues were refolded according to the method of example 6 utilizing a cystamine adduct forming compound and a refolding solution comprising 2 mM cysteine. Each refolding procedure utilized a thaumatin-cystaamine adduct at a concentration of 20 μg/ml. The natural plant thaumatin I had a refolding effilciency of 19-25% while the [Asp$^{113}$] thaumatin I analogue had a refolding efficiency of about 1%. The [Lys$^{46}$, Asp$^{113}$] thaumatin I analogue had an intermediate refolding effiency in this set of experiments of about 5%. Only the natural plant thaumatin I and the [Lys$^{46}$, Asp$^{113}$] analogue elicited a sweet taste upon testing of the unconcentrated materials. Upon concentration, all three materials elicited sweet tastes.

TABLE 3

| Example No. | Thaumatin Type | RIA Reacted (μg/ml) | Refolded Protein/ Starting Protein (%) | Sweetness |
| --- | --- | --- | --- | --- |
| 17 | Plant | 3.7 | 19 | + |
| 18 | Plant | 5.0 | 25 | + |
| 19 | [Asp$^{113}$] | 0.08 | 0.4 | + |
| 20 | [Asp$^{113}$] | 0.29 | 1.5 | + |
| 21 | [Lys$^{46}$, Asp$^{113}$] | 0.8 | 4 | + |
| 22 | [Lys$^{46}$, Asp$^{113}$] | 1.3 | 7 | + |

Numerous modifications and variations in practice of the invention as illustrated in the following examples are expected to occur to those skilled in the art. As one example, it is contemplated that certain polypeptide analogues may be correctly refolded by the above-described invention. Consequently, only such limitations should be placed on the invention as appear in the following claims.

What is claimed is:

1. A method for establishing a biologically active native conformation in a polypeptide containing multiple disulfide bonds comprising the steps:
   (1) treating the polypeptide with (a) a denaturing agent and (b) a reducing agent capable of reductively dissociating disulfide bonds;
   (2) concurrently reducing the concentration of the reducing agent while forming a stable intermediate by reacting a disulfide-group containing compound with the reduced cysteine moieties of the polypeptide; and
   (3) forming native disulfide bonds in the presence of a mild oxidizing/reducing environment while dissociating the disulfide-group polypeptide moieties.

2. The method of claim 1 wherein reducing agent is removed concurrently with formation of a stable intermediate in a gel filtration column.

3. The method of claim 1 wherein the polypeptide containing multiple disulfide bonds is thaumatin.

4. The method of claim 2 wherein the polypeptide containing multiple disulfide bonds is thaumatin.

5. The method of claim 4 wherein the denaturing agent is urea.

6. The method of claim 4 wherein the reducing agent is $\beta$-mercaptoethanol.

7. The method of claim 4 wherein the disulfide-group containing compound is a member of the group consisting of cystamine, oxidized glutathione and cystine.

8. The method of claim 4 wherein the mild oxidizing/reducing environment is a solution comprising a weak reducing agent and a weak oxidizing agent.

9. The method of claim 8 wherein the weak reducing agent is selected from the group consisting of cysteine, reduced glutathione and cysteamine.

10. The method of claim 8 wherein the weak oxidizing agent is selected from the group consisting of atmospheric oxygen, cystine, oxidized glutathione and cystamine.

11. The method of claim 4 wherein the mild oxidizing/reducing environment is characterized by a pH of 7 to 9.

12. The method of claim 4 wherein the denaturing agent is urea, the reducing agent is $\beta$-mercaptoethanol, the disulfide-group containing compound is cystamine and the mild oxidizing/reducing environment is a solution comprising cysteine and atmospheric oxygen with a pH of 7 to 9.

* * * * *

UNITED STATES PATENT AND TRADEMARK OFFICE
CERTIFICATE OF CORRECTION

PATENT NO. : 4,766,205

DATED : August 23, 1988

INVENTOR(S) : Ghosh-Dastidar

It is certified that error appears in the above-identified patent and that said Letters Patent is hereby corrected as shown below:

Abstract, line 4, change "conformation" to --conformations--;

abstract, line 13, change "moeities" to --moieties--;

column 7, line 55, change "Tris-HC" to --Tris-HCl--;

column 7, line 66, change "moeities" to --moieties--;

column 8, line 39, change "HC" to --HCl--;

column 8, line 46, change "20 µaliquots" to --20 µl aliquots--;

column 9, line 31, change "Thauamtin" to --Thaumatin--;

column 10, line 39, change "moeities" to --moieties--;

column 12, line 43, change "thaumatin-cystaamine" to --thaumatin-cystamine--;

column 12, line 45, change "effilciency" to --efficiency--.

Signed and Sealed this

Seventeenth Day of January, 1989

Attest:

DONALD J. QUIGG

*Attesting Officer*  *Commissioner of Patents and Trademarks*